United States Patent
Appéré et al.

(10) Patent No.: US 6,265,436 B1
(45) Date of Patent: *Jul. 24, 2001

(54) SUBSTITUTED 5-BIPHENYL-3,4-DIHYDROXY-2(5H)-FURANONES AND METHOD OF USE THEREFOR

(75) Inventors: Georges Appéré, Sucy-en-Brie; Irene Erdelmeier, Paris; Claire Banissi, Vincennes; Marc Moutet, Bagneux, all of (FR); Allen Hopper, Cranberry, NJ (US)

(73) Assignee: Oxis Therapeutics Inc., Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/406,544

(22) Filed: Sep. 27, 1999

Related U.S. Application Data

(63) Continuation-in-part of application No. 08/915,099, filed on Aug. 20, 1997, now Pat. No. 6,005,000.
(60) Provisional application No. 60/024,440, filed on Aug. 22, 1996, and provisional application No. 60/024,586, filed on Aug. 26, 1996.

(51) Int. Cl.[7] .................. A61K 31/365; C07D 307/62
(52) U.S. Cl. .................. 514/473; 514/336; 514/444; 546/284.4; 549/60; 549/315
(58) Field of Search ............... 549/315, 60; 546/284.4; 514/473, 336, 444

(56) References Cited

U.S. PATENT DOCUMENTS

| | | | |
|---|---|---|---|
| 5,071,872 | 12/1991 | Witiak et al. | 514/465 |
| 5,095,126 | 3/1992 | Witiak et al. | 549/315 |
| 5,185,366 | 2/1993 | Witiak et al. | 514/456 |
| 5,288,751 | 2/1994 | Brooks et al. | 514/438 |
| 5,298,526 | 3/1994 | Witiak et al. | 514/473 |
| 5,399,721 | 3/1995 | Hopper et al. | 549/60 |
| 5,504,107 | 4/1996 | Mantri et al. | 514/473 |
| 5,504,108 | 4/1996 | Witiak et al. | 514/473 |
| 5,534,540 | 7/1996 | Ulrich et al. | 514/473 |
| 6,005,000 * | 12/1999 | Hopper et al. | 514/473 |

FOREIGN PATENT DOCUMENTS

| | | |
|---|---|---|
| 4-29985 | 1/1992 | (JP) . |
| WO 95/32194 | 11/1995 | (WO) . |

OTHER PUBLICATIONS

Mak et al, Biochemical Pharmacology, vol. 55, p.1921–1926, Jun. 1998.*
Chem. Abstracts, vol. 126:74689: Kwon et al Yakhak Hoechi , vol. 40 (5), p. 539–544 (1996).*
Alami et al, 1993, Tetrahedron Lett 34:6403–6.
Berson and Greenbaum, 1958, J Am Chem Soc 80:653–6.
Bisby et al, 1995, Free Rad Biol Med 20:411–20.
Boopathy and Baiasubramanian, 1968, Biochem J 239:371–7.
Brown, 1975, Organic Syntheses via Boranes, John Wiley and Sons, New York, 100, 178.
Buckle and Fenwick, 1989, J Chem Soc Perkin Trans 1:477–82.
Buffinton and Doe, 1995, Free Rad Biol Med 19:911–8.
Bundy et al, 1995, J Med Chem 38:4161–3.
Coyle et al, 1993, Science 262:689–95.
DeJarlais et al, 1980, Synth Commun 10:653–60.
Egan and Gale, 1985, J Biol Chem 260; 11554–9.
Evans et al, 1987, Biochem Pharm 36:2035–7.
Frimer et al, 1995, J Org Chem 60:4510–20.
Grisar et al, 1995, J Med Chem 38:453–8.
Gross et al, 1994, Hepato–Gastroenterol 41:320–7.
Halliwell, 1987, FASEB J 1:358–64.
Halliwell, 1991, Drugs 42:569–605.
Hopper et al. (1995) J. Org. Chem. 60:3334–41.
Hvoslef and Pedersen, 1979, Acta Chemica Scand B 33:503–11.
Kato et al, 1988, J Med Chem 31:793–8.
Kerwin, 1995, J Med Chem 38:4343–62.
King and Burns, 1975, the Second conference on Vitamin C, the New York Academy of Science, New York.
Lafont et al, 1995, J Clin Invest 95:1018–25.
Mansuy et al, 1996, Biochem Biophys Res Comm 135:1015–21.
Mantri and Witiak, 1994, Curr Med Chem 1:328–55.
Marshall et al, 1986, J Org Chem 51:858–63.
Maxwell, 1995, Drugs 49:345–61.
Millar et al, 1996, J Org Chem 51:4726–8.
Nicolaou and Webber, 1984, J Chem Soc, Chem Commun 350–1.
Nihro et al, 1992, J Med Chem 35:1618–23.
Nunes et al, 1995, Thromb Vasc Biol 15:156–65.
Ochiai et al, 1991,J Am Chem Soc 113:1319–23.
O'Sullivan et al, 1992, Biochem Biophys Res Comm 187:1123–7.
Rabinovici et al, 1993, J Appl Physiol 74:1791–802.
Remacle et al, 1995, Mutat Res 316:103–22.

(List continued on next page.)

Primary Examiner—Bernard Dentz
(74) Attorney, Agent, or Firm—Klauber & Jackson

(57) ABSTRACT

The present invention broadly relates to racemic or optically active 5-substituted 3,4-dihydroxy-2(5H)-furanone compounds and their pharmaceutically acceptable salts, useful for treating a pathology in which reactive oxygen species and inflammatory mediators are contributing deleterious factors, such as acute or chronic inflammatory disorders, for example, asthma, rheumatoid arthritis, inflammatory bowel disease, and acute respiratory distress syndrome; neurodegenerative disorders, such as Alzheimer disease, Parkinson disease, amyotrophic lateral sclerosis, traumatic brain injury and multiple sclerosis; cardiovascular diseases, such as atherosclerosis; viral diseases, such as AIDS; skin diseases, such as psoriasis, sunburn and premature aging; and eye diseases, such as glaucoma, cataract, senile macular degeneration, inflammatory eye conditions, trauma, post-traumatic eye disorders, diabetic retinopathy, and eye infections.

35 Claims, No Drawings

OTHER PUBLICATIONS

Saeva et al, 1991, J Am Chem Soc 113:5333–7.
Schank, 1972, Synthesis 176–90.
Schreck et al, 1992, Free Rad Res Comms 17:221–37.
Shimuzu et al, 1984, Pro Natl Acad Sci USA 81:689–93.
Silverman, 1992, The Organic Chemistry of Drug Design and Drug Action, Academic Press, San Diego, CA, 19–20.
Steinberg, 1995, Lancet 346:36–8.
Stork and Rychnovsky, 1987, J Am Chem Soc 109:1564–5.
Sun, 1990, Free Rad Biol & Med 8:583–99.
Triozzi et al, 1993, Int J Immunopharmac 15:47–54.
Wang et al, 1996, Pharm Exp Therap 277:714–20.
Wimalasena et al, 1994, Biochem Biophys Res Comm 200:113–9.
Witiak et al, 1982, J Med Chem 25:90–3.
Witiak et al, 1986, J Med Chem 29:2170–4.
Witiak et al, 1987, J Org Chem 52:2324–7.
Witiak et al, 1987, Actual Chim Therap15:41–62.
Witiak et al, 1988, J Med Chem 1:328–55.
Witiak et al, 1988, J Med Chem 31:1437–45.
Witiak et al, 1992, in Trends in Medicinal chemistry '90, Proceeding of the XIth International Symposiumon Medicinal Chemistry, Jerusalem, Israel, Sep. 2–7, Sarel et al eds. Blackwell Scientific Publicstions, Oxford, London :243–56.
Database WPI, Week 9221, Derwent Publications Ltd., London, GB. AN 92–085896, JP 04 029 985 A (Meiji Seika Kaisha), Jan. 31, 1992, See abs.
Hopper et al., 1995, J. Org. Chem., 60:3334–41.

* cited by examiner

SUBSTITUTED 5-BIPHENYL-3,4-DIHYDROXY-2(5H)-FURANONES AND METHOD OF USE THEREFOR

CROSS-REFERENCE TO RELATED APPLICATION

This application is a Continuation-in-part of Ser. No. 08/915,099, filed Aug. 20, 1997 now U.S. Pat. No. 6,005,000 which claims priority from Provision Application 60/024,440 filed Aug. 22, 1996 and 60/024,586 filed Aug. 26, 1996.

FIELD OF THE INVENTION

The invention relates generally to substituted 5-biphenyl-3,4-dihydroxy-2(5H)-furanones, methods of preparation therefor, and method of use thereof.

BACKGROUND OF THE INVENTION

The aci-reductone 4-(4-chlorophenyl)-2-hydroxytetronic acid compound (CHTA) possesses antilipidemic and antiaggregatory properties which differ from those of the classical phenoxyactetic acids as has been disclosed in Witiak et at. *J. Med. Chem.*, 1988, 31:1434–1445 and Kamanna et al., *Lipids,* 1989, 24:25–32. Although unsubstituted 2-alkyl- and 2-acyltetronic acids are frequently found in nature, the 2-hydroxy-substituted tetronic acid redox system is found only in vitamin C and its closely related relatives (isoascorbic acid, erythroascorbic acid) and derivatives, and the macrolide antibiotic, chlorothricin.

The antiaggregatory activities of 2-hydroxytetronic acid aci-reductone compound (CHTA) are of interest since blood platelets are involved in the genesis of atherosclerosis. 2-Hydroxytetronic acid aci-reductones inhibit collagen-induced human platelet aggregation and secretion of [$^{14}$C]-serotonin in a concentration-dependent manner at equivalent doses, as reported in Witiak et al., *J. Med. Chem.,* 1982, 25:90–93. The CHTA compound inhibits platelet function by a similar mechanism, involving arachidonic acid release. Redox analogues, such as 2-hydroxytetronic acid, function as antioxidants in membranes or interfere with free radical processes involved in the biosynthetic elaboration of cyclic prostaglandin endoperoxides (PGG$_2$ and PGH$_2$), and, subsequently, thromboxane A$_2$ from arachidonic acid.

The development of dual antioxidant-arachidonic acid (AA) metabolism inhibitors may provide added benefits over existing drugs for the treatment of diseases associated with oxidative stress and inflammation. Numerous conditions including asthma, rheumatoid arthritis, irritable bowel disease (IBD), adult respiratory distress syndrome (ARDS), atherosclerosis, ischemia/reperfusion injury, restenosis, neurodegenerative disorders and initiation and promotion of carcinogenesis correlate with abnormally high levels of reactive oxygen species (ROS). Antioxidant-based therapies including both natural antioxidants (e.g., vitamin E, vitamin C and SOD), and synthetic antioxidants (e.g., 4-aryl-2-hydroxytetronic acids, 2-O-alkyl ascorbic acids, probucol and tirilazad mesylate) have been, or are currently being, investigated for the treatment of a number of these conditions.

Previously, the S-arachidonic acid aci-reductone analog (S)-3,4-dihydroxy-5 [(all Z)-3,6,9,12-octadecatraenyl]-2(5H)-furanone, was identified as a stereoselective and potent arachidonic acid metabolic inhibitor. This compound inhibits both PGE$_2$ and LTB$_4$ production in stimulated macrophages (IC$_{50}$=20 μM) and blocks AA-induced platelet aggregation (AAIPA) with an IC$_{50}$<10 μM. Dual cyclooxygenase (COX) and lipoxygenase (LO) activity could be important in preventing substrate shunting in the arachidonic acid cascade. Although this compound demonstrates an encouraging biological profile, both its instability and labored synthesis render this compound less than satisfactory as a therapeutic agent.

U.S. application Ser. No. 08/915,099, and PCT/US97/14878, incorporated herein by reference, describe 5-substituted and 5,5-disubstituted-3,4-dihydroxy-2(5H)-furanones, including 5-unsubstituted biphenyl derivatives which have antilipidemic, antiaggregatory, and antiinflammatory activities useful for the treatment of various conditions and diseases in humans and animals.

There exists a need for new therapeutic agents which exhibit the aforementioned activities. It is to this aim that the present invention is directed.

The citation of any reference herein should not be construed as an admission that such reference is available as "Prior Art" to the instant application.

SUMMARY OF THE INVENTION

The present invention broadly relates to racemic or optically active compounds of the formula I:

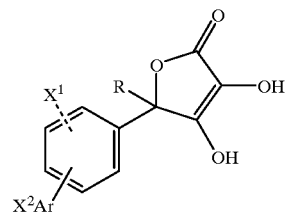

wherein R is hydrogen, a lower alkyl group optionally substituted by one or more halo groups, a cycloalkyl group, or an aryl group optionally substituted by one or more halo, alkyl of one to eight carbon atoms, alkoxy of one to eight carbon atoms, cycloalkyl, nitro or trifluoromethyl groups; X$^1$ is optionally one or more halo, alkyl of one to eight carbon atoms, alkoxy of one to eight carbon atoms, cycloalkyl, nitro or trifluoromethyl groups; and Ar is an aromatic or heteroaromatic ring substituted by X$^2$, X$^2$ being one or more halo, alkyl of one to eight carbon atoms, alkoxy of one to eight carbon atoms, cycloalkyl, nitro or trifluoromethyl groups; or a pharmaceutically acceptable salt thereof.

The substituted aromatic group Ar may be, for example, phenyl or naphthyl, substituted by one or more halo, alkyl of one to eight carbon atoms, alkoxy of one to eight carbon atoms, cycloalkyl, nitro or trifluoromethyl groups. The substituted heteroaromatic group may contain 4–10 ring members and 1–3 heteroatoms selected from the group consisting of oxygen, nitrogen and sulfur, for example, a thienyl, furyl, or pyridyl ring. The compounds herein may be racemic or optically active, such as the (S) or (R) enantiomers.

In a further broad aspect of the invention, methods of treating a pathology in which reactive oxygen species and inflammatory mediators are contributing deleterious factors are provided which comprises administration to a patient in need of such therapy an effective amount of a racemic or optically active compound of the formula I:

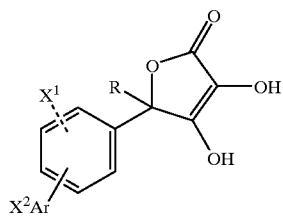

wherein R is hydrogen, a lower alkyl group optionally substituted by one or more halo groups, a cycloalkyl group, or an aryl group optionally substituted by one or more halo, alkyl of one to eight carbon atoms, alkoxy of one to eight carbon atoms, cycloalkyl, nitro or trifluoromethyl groups; $X^1$ is optionally one or more halo, alkyl of one to eight carbon atoms, alkoxy of one to eight carbon atoms, cycloalkyl, nitro or trifluoromethyl groups; and Ar is an aromatic or heteroaromatic ring substituted by $X^2$, $X^2$ being one or more halo, alkyl of one to eight carbon atoms, alkoxy of one to eight carbon atoms, cycloalkyl, nitro or trifluoromethyl groups; or a pharmaceutically acceptable salt thereof.

The invention further encompasses pharmaceutical compositions comprising the above-mentioned compounds and a pharmaceutically acceptable carrier. Pathologies treatable using the compounds described herein include acute or chronic inflammatory disorders, such as by way of non-limiting example, asthma, rheumatoid arthritis, inflammatory bowel disease, or acute respiratory distress syndrome. The pathology may be a neurodegenerative disorders, such as but not limited to Alzheimer disease, Parkinson disease, amyotrophic lateral sclerosis, traumatic brain injury or multiple sclerosis. In a further embodiment, the pathology comprises cardiovascular disease, such as atherosclerosis. In yet a further embodiment, the pathology comprises a viral disease, such as but not limited to AIDS. In still yet a further embodiment, the pathology comprises a skin disease, such as psoriasis, sunburn and premature aging. In yet another embodiment, the pathology comprises an eye disease, such as but not limited to glaucoma, cataract, senile macular degeneration, inflammatory eye conditions, trauma, post-traumatic eye disorders, diabetic retinopathy, and eye infections.

These and other aspects of the present invention will be better appreciated by reference to the following Detailed Description.

DETAILED DESCRIPTION OF THE INVENTION

The present invention is directed to compounds of the general formula I

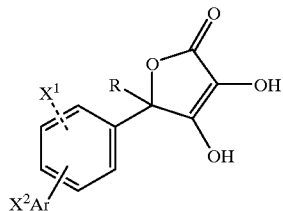

wherein R is hydrogen, a lower alkyl group optionally substituted by one or more halo groups, a cycloalkyl group, or an aryl group optionally substituted by one or more halo, alkyl of one to eight carbon atoms, alkoxy of one to eight carbon atoms, cycloalkyl, nitro or trifluoromethyl groups; $X^1$ is optionally one or more halo, alkyl of one to eight carbon atoms, alkoxy of one to eight carbon atoms, cycloalkyl, nitro or trifluoromethyl groups; and Ar is an aromatic or heteroaromatic ring substituted by $X^2$, $X^2$ being one or more halo, alkyl of one to eight carbon atoms, alkoxy of one to eight carbon atoms, cycloalkyl, nitro or trifluoromethyl groups; or a pharmaceutically acceptable salt thereof.

The compounds of formula I can be formed as mixtures of enantiomers, due to the asymmetric carbon atoms of the furanone ring structure. The present invention contemplates the use of both the individual enantiomers, as well as the racemate.

As used herein, the term lower "alkyl" means straight- or branched-chain saturated aliphatic hydrocarbon groups preferably containing 1–6 carbon atoms. Representative of such groups are methyl, ethyl, isopropyl, isobutyl, butyl, pentyl, hexyl and the like. The term "alkoxy" means a lower alkyl group as defined above attached to the remainder of the molecule by oxygen. Examples of alkoxy include methoxy, ethoxy, propoxy, isopropoxy and the like. The term "cycloalkyl" refers to cyclic alkyl groups with three up to about 8 carbons, including for example cyclopropyl, cyclobutyl, cyclohexyl and the like. The term "aromatic ring" refers to phenyl and naphthyl groups. The term "heteraromatic ring" refers to heterocyclic groups containing 4–10 ring members and 1–3 heteroatoms selected from the group consisting of oxygen, nitrogen and sulfur. Examples include but are not limited to isoxazolyl, phenylisoxazolyl, furyl, pyrimidinyl, quinolyl, tetrahydroquinolyl, pyridyl, imidazolyl, pyrrolidinyl, 1,2,4-triazoylyl, thiazolyl, thienyl, and the like. The aromatic or heteroaromatic group may be attached to the 5-phenyl group at any suitable position on either group, for example, in the case of naphthyl, at its 1 or 2 position; in the case of thienyl, at its 2 or 3 position; in the case of furyl, at its 2 or 3 position, and in the case of pyridyl, at its 2, 3 or 4 position; and likewise to any suitable position on the 5-phenyl group.

The invention also provides for pharmaceutical compositions comprising the compounds of formula I above, as well as their physiologically acceptable salts, such as, for example, $Na^+$, $K^+$, and $NH_4^+$.

Examples of R groups other than hydrogen include straight or branched-chain alkyl groups of 1 to 8 carbon atoms such as methyl, ethyl, isopropyl, butyl, isobutyl, t-butyl, pentyl, hexyl, and the like. The lower alkyl group may be substituted by one or more halo groups, for example, chloromethyl, 2-chloroethyl, trifluoromethyl, etc., or substituted by alkyl, alkoxy, cycloalkyl, nitro or trifluoromethyl. R may also be an aryl group such as the aromatic or heteroaromatic groups described hereinabove, optionally substituted by one or more halo, alkyl, alkoxy, cycloalkyl, nitro or trifluoromethyl groups, or various combinations thereof.

$X^1$ represent one or more optional substituents off the 5-phenyl ring, and thus is indicated in the above formula as a dashed line. $X^1$ may be one or more halo groups, such as fluoro, bromo or chloro; one or more straight- or branched-chain alkyl group of one to eight carbon atoms as described above; an alkoxy group of one to eight carbons, such as those described above; a cycloalkyl group as described above, a nitro group or a trifluoromethyl group. Wherein $X^1$ represents more than one substituent, various combinations of the foregoing substituents are embraced in the present invention.

The following formulas set forth illustrative examples of the compounds of the present invention with various substituted Ar groups, the substituent or substituents thereon represented by $X^2$.

In one embodiment, Ar represents a substituted phenyl or 1-naphthyl group, as shown in formula IIa and IIb:

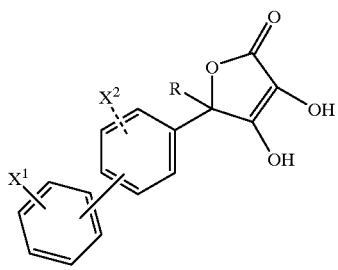

IIa

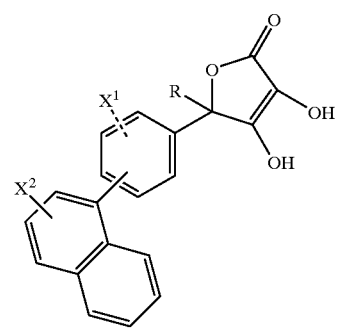

IIb

In formulas IIa and IIb, $X^1$ is as defined hereinabove. $X^2$ represents one or more halo, alkyl of one to eight carbon atoms, alkoxy of one to eight carbon atoms, cycloalkyl, nitro or trifluoromethyl groups. The naphthyl group may be attached at position 2, or position 1 as shown in the example.

Examples of compounds of formula IIa wherein Ar is a substituted phenyl group and $X^1$ is H include but are not limited to 5-[(4'-fluoro-1,1'-biphenyl)-4-yl]-3,4-dihydroxy-2(5H)-furanone;

5-[(4'-fluoro-1,1'-biphenyl)-4-yl]-5-methyl-3,4-dihydroxy-2(5H)-furanone;

5-[(4'-fluoro-1,1'-biphenyl)-4-yl]-5-phenyl-3,4-dihydroxy-2(5H)-furanone;

5-[(4'-fluoro-1,1'-biphenyl)-4-yl]-5-cyclohexyl-3,4-dihydroxy-2(5H)-furanone;

5-[(4'-fluoro-1,1'-biphenyl)-4-yl]-5-(4-nitrophenyl)-3,4dihydroxy-2(5H)-furanone;

5-[(4'-bromo-1,1'-biphenyl)-4-yl]-5-methyl-3,4-dihydroxy-2(5H)-furanone;

5-[(4'-chloro-1,1'-biphenyl)-4-yl]-5-methyl-3,4-dihydroxy-2(5H)-furanone;

5-[(2',4'-dichloro-1,1'-biphenyl)-4-yl]-3,4-dihydroxy-2(5H)-furanone;

5-[(2',4'-dichloro-1,1'-biphenyl)-4-yl]-5-methyl-3,4-dihydroxy-2(5H)-furanone;

5-[(4'-chloro-1,1'-biphenyl)-4- yl]-5-phenyl-3,4-dihydroxy-2(5H)-furanone;

5-[(4'-trifluoromethyl-1,1'-biphenyl)-4-yl]-3,4-dihydroxy-2(5H)-furanone;

5-[(4'-trifluoromethyl-1,1'-biphenyl)-4-yl]-5-methyl-3,4-dihydroxy-2(5H)-furanone;

5-[(4'-trifluoromethyl-1,1'-biphenyl)-4-yl]-5-phenyl-3,4-dihydroxy-2(5H)-furanone;

5-[(4'-trifluoromethyl-1,1'-biphenyl)-4-yl]-5-cyclohexyl-3,4-dihydroxy-2(5H)-furanone;

5-[(4'-trifluoromethyl-1,1'-biphenyl)-4-yl]-5-(4-methylphenyl)-3,4-dihydroxy-2(5H)-furanone;

5-[(4'-trifluoromethyl-1,1'-biphenyl)-4-yl]-5-(4-methoxyphenyl)-3,4-dihydroxy-2(5H)-furanone;

5-[(4'-nitro-1,1'-biphenyl)-4-yl]-3,4-dihydroxy-2(5H)-furanone;

5-[(4'-nitro-1,1'-biphenyl)-4-yl]-5-ethyl-3,4-dihydroxy-2(5H)-furanone;

5-[(4'-nitro-1,1'-biphenyl)-4-yl]-5-phenyl-3,4-dihydroxy-2(5H)-furanone;

5-[(4'-nitro-1,1'-biphenyl)-4-yl]-5-cyclohexyl-3,4-dihydroxy-2(5H)-furanone;

5-[(4'-nitro-1,1'-biphenyl)-4-yl]-5-(4-trifluoromethylphenyl)-3,4-dihydroxy-2(5H)-furanone;

5-[(4'-cyclohexyl-1,1'-biphenyl)-4-yl]-3,4-dihydroxy-2(5H)-furanone;

5-[(4'-cyclohexyl-1,1'-biphenyl)-4-yl]-5-methyl-3,4-dihydroxy-2(5H)-furanone;

5-[(4'-cyclohexyl-1,1'-biphenyl)-4-yl]-5-phenyl-3,4-dihydroxy-2(5H)-furanone;

5-[(4'-cyclohexyl-1,1'-biphenyl)-4-yl]-5-cyclopentyl-3,4-dihydroxy-2(5H )-furanone;

5-[(4'-cyclohexyl-1,1'-biphenyl)-4-yl]-5-(4-ethoxyphenyl)-3,4-dihydroxy-2(5H)-furanone;

5-[(4'-methyl-1,1'-biphenyl)-4-yl]-3,4-dihydroxy-2(5H)-furanone;

5-[(4'-methyl-1,1'-biphenyl)-4-yl]-5-methyl-3,4-dihydroxy-2(5H )-furanone;

5-[(2',4'-dimethyl-1,1'-biphenyl)-4-yl]-3,4-dihydroxy-2(5H)-furanone;

5-[(2',4'-dimethyl-1,1'-biphenyl)-4-yl]-5-methyl-3,4-dihydroxy-2(5H)-furanone;

5-[(2',4'-dimethyl-1,1'-biphenyl)-4-yl]-5-phenyl-3,4-dihydroxy-2(5H)-furanone;

5-[(4'-methyl-1,1'-biphenyl)-4-yl]-5-(2-chloropropyl)-3,4-dihydroxy-2(5H )-furanone;

5-[(4'-methyl-1,1'-biphenyl)-4-yl]-5-cyclopropyl-3,4-dihydroxy-2(5H)-furanone;

5-[(4'-methyl-1,1'-biphenyl)-4-yl]-5-phenyl-3,4-dihydroxy-2(5H)-furanone;

5-[(4'-ethyl-1,1'-biphenyl)-4-yl]-5-phenyl-3,4-dihydroxy-2(5H)-furanone;

5-[(4'-methoxy-1,1'-biphenyl)-4-yl]-3,4-dihydroxy-2(5H)-furanone;

5-[(4'-methoxy-1,1'-biphenyl)-4-yl]-5-methyl-3,4-dihydroxy-2(5H)-furanone;

5-[(4'-methoxy-1,1'-biphenyl)-4-yl]-5-chloromethyl-3,4-dihydroxy-2(5H)-furanone; and 5-[(4'-methoxy-1,1'-biphenyl)-4-yl]-5-phenyl-3,4-dihydroxy-2(5H)-furanone.

Examples of compounds of formula IIa wherein $X^1$ is other than H include:

5-[(3,4'-dichloro-1,1'-biphenyl)-4-yl]-3,4-dihydroxy-2(5H)-furanone;

5-[(3,4'-dichloro-1,1'-biphenyl)-4-yl]-5-methyl-3,4-dihydroxy-2(5H)-furanone;

5-[(3,4'-dichloro-1,1'-biphenyl)-4-yl]-5-phenyl-3,4-dihydroxy-2(5H)-furanone;

5-[(3,4'-dichloro-1,1'-biphenyl)-4-yl]-5-cyclohexyl-3,4-dihydroxy-2(5H)-furanone;

5-[(3,4'-dichloro-1,1'-biphenyl)-4-yl]-5-(4-nitrophenyl)-3,4-dihydroxy-2(5H)-furanone;

5-[(3,4'-dimethyl-1,1'-biphenyl)-4-yl]-3,4-dihydroxy-2(5H)-furanone;

5-[(3,4'-dimethyl-1,1'-biphenyl)-4-yl]-5-methyl-3,4-dihydroxy-2(5H)-furanone;

5-[(3,4'-dimethyl-1,1'-biphenyl)-4-yl]-5-phenyl-3,4-dihydroxy-2(5H)-furanone;

5-[(3,4'-dimethyl-1,1'-biphenyl)-4-yl]-5-cyclohexyl-3,4-dihydroxy-2(5H)-furanone;

5-[(3,4'-dimethyl-1,1'-biphenyl)-4-yl]-5-(4-nitrophenyl)-3,4-dihydroxy-2(5H)-furanone;

5-[(3-chloro-4'-methyl-1,1'-biphenyl)-4-yl]-3,4-dihydroxy-2(5H)-furanone;

5-[(3-chloro-4'-methyl-1,1'-biphenyl)-4-yl]-5-methyl-3,4-dihydroxy-2(5H)-furanone;

5-[(3-chloro-4'-methyl-1,1'-biphenyl)-4-yl]-5-phenyl-3,4-dihydroxy-2(5H)-furanone;

5-[(3-chloro-4'-methyl-1,1'-biphenyl)-4-yl]-5-cyclohexyl-3,4-dihydroxy-2(5H)-furanone; and 5-[(3-chloro-4'-methyl-1,1'-biphenyl)-4-yl]-5-(4-nitrophenyl)-3,4-dihydroxy-2(5H)-furanone;

Examples of compounds of formula IIb include but are not limited to

5-[4-(1-(2-chloronaphthyl))phenyl]-3,4-dihydroxy-2(5H)-furanone;

5-[4-(1-(2,5-dichloronaphthyl))phenyl]-3,4-dihydroxy-2(5H)-furanone;

5-[4-(1-(2-chloronaphthyl))phenyl]-5-methyl-3,4-dihydroxy-2(5H)-furanone;

5-[4-(2-(6-methylnaphthyl))phenyl]-5-methyl-3,4-dihydroxy-2(5H)-furanone;

5-[4-(3-(3-methylnaphthyl))phenyl]-5-methyl-3,4-dihydroxy-2(5H)-furanone;

5-[4-(2-(1-methylnaphthyl))phenyl]-5-methyl-3,4-dihydroxy-2(5H)-furanone;

5-[4-(1-(2-chloronaphthyl))phenyl]-5-phenyl-3,4-dihydroxy-2(5H)-furanone;

5-[4-(1-(2-chloronaphthyl))phenyl]-5-cyclohexyl-3,4-dihydroxy-2(5H)-furanone;

5-[4-(1-(2-chloronaphthyl))phenyl]-5-(4-toluyl)-3,4-dihydroxy-2(5H)-furanone;

5-[4-(1-(3-methylnaphthyl))phenyl]-5-(4-anisoyl)-3,4-dihydroxy-2(5H)-furanone;

5-[4-(1-(3-methylnaphthyl))phenyl]-5-ethyl-3,4-dihydroxy-2(5H)-furanone;

5-[4-(1-(3-methylnaphthyl))phenyl]-5-nitrophenyl-3,4-dihydroxy-2(5H)-furanone; and 5-[4-(1-(3-methylnaphthyl))phenyl]-5-(4-chlorophenyl)-3,4-dihydroxy-2(5H)-furanone.

In another embodiment, Ar represents a substituted heteroaromatic group, such as a 2-thienyl group as shown in formula III:

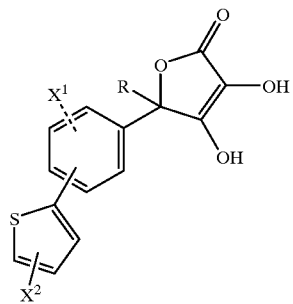

The thienyl group may be attached at position 2, as shown in formula III above, or at position 3. $X^1$ is as defined hereinabove. $X^2$ represents one or more halo, alkyl of one to eight carbon atoms, alkoxy of one to eight carbon atoms, cycloalkyl, nitro or trifluoromethyl groups. Examples include but are not limited to 5-[(4-(5-methylthien)-2-yl)phenyl]-3,4-dihydroxy-2(5H)-furanone;

5-[(4-(5-methylthien)-2-yl)phenyl]-5-methyl-3,4-dihydroxy-2(5H)-furanone;

5-[(4-(5-methylthien)-2-yl)phenyl]-5-phenyl-3,4-dihydroxy-2(5H)-furanone;

5-[(4-(5-methylthien)-2-yl)phenyl]-5-(4-nitrophenyl)-3,4-dihydroxy-2(5H)-furanone;

5-[(3-(4-chlorothien)-2-yl)phenyl]-5-methyl-3,4-dihydroxy-2(5H)-furanone;

5-[(4-(4-chlorothien)-2-yl)phenyl]-5-phenyl-3,4-dihydroxy-2(5H)-furanone;

5-[(3-(4-methoxythien)-2-yl)phenyl]-5-methyl-3,4-dihydroxy-2(5H)-furanone;

5-[(4-(5-cyclohexylthien)-3-yl)phenyl]-5-methyl-3,4-dihydroxy-2(5H)-furanone;

5-[(3-(2-trifluoromethylthien)-3-yl)phenyl]-5-methyl-3,4-dihydroxy-2(5H)-furanone; and 5-[(2-(5-chlorothien)-3-yl)phenyl]-5-methyl-3,4-dihydroxy-2(5H)-furanone.

As noted above, the phenyl group may be optionally substituted, with $X^1$ as hereinbefore defined. Examples include:

5-[(4-(5-methylthien)-2-yl)2-chlorophenyl]-3,4-dihydroxy-2(5H)-furanone;

5-[(4-(5-methylthien)-2-yl)3-methylphenyl]-5-methyl-3,4-dihydroxy-2(5H)-furanone;

5-[(4-(5-methylthien)-2-yl)2-trifluoromethylphenyl]-5-phenyl-3,4-dihydroxy-2(5H)-furanone;

5-[(4-(5-methylthien)-2-yl)3-fluorophenyl]-5-(4-nitrophenyl)-3,4-dihydroxy-2(5H)-furanone;

5-[(3-(4-chlorothien)-2-yl)2-methoxyphenyl]-5-methyl-3,4-dihydroxy-2(5H)-furanone;

5-[(4-(4-chlorothien)-2-yl)3-ethylphenyl]-5-phenyl-3,4-dihydroxy-2(5H)-furanone;

5-[(3-(4-methoxythien)-2-yl)5-chlorophenyl]-5-methyl-3,4-dihydroxy-2(5H)-furanone;

5-[(4-(5-cyclohexylthien)-3-yl)3-bromophenyl]-5-methyl-3,4-dihydroxy-2(5H)-furanone;

5-[(3-(2-trifluoromethylthien)-3-yl)2-fluorophenyl]-5-methyl-3,4-dihydroxy-2(5H)-furanone; and 5-[(2-(5-chlorothien)-3-yl)4-cyclohexylphenyl]-5-methyl-3,4-dihydroxy-2(5H)-furanone.

Another embodiment wherein Ar represents a substituted heteroaromatic group is a 2-furyl group, as shown in formula IV:

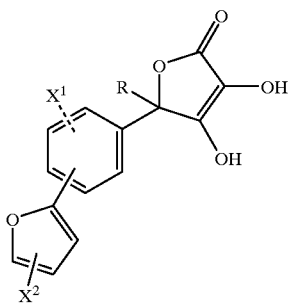

The furyl group may be attached at position 2, as shown, or at position 3. $X^1$ is as defined hereinabove. $X^2$ represents one or more halo, alkyl of one to eight carbon atoms, alkoxy of one to eight carbon atoms, cycloalkyl, nitro or trifluoromethyl groups. Examples include but are not limited to 5-[(4-(5-methylfur)-2-yl)phenyl]-3,4-dihydroxy-2(5H)-furanone;

5-[(4-(5-methylfur)-2-yl)phenyl]-5-methyl-3,4-dihydroxy-2(5H)-furanone;

5-[(4-(5-methylfur)-2-yl)phenyl]-5-phenyl-3,4-dihydroxy-2(5H)-furanone;

5-[(4-(5-methylfur)-2-yl)phenyl]-5-(4-nitrophenyl)-3,4-dihydroxy-2(5H)-furanone;

5-[(3-(4-chlorofur)-2-yl)phenyl]-5-methyl-3,4-dihydroxy-2(5H)-furanone;

5-[(4-(4-chlorofur)-2-yl)phenyl]-5-phenyl-3,4-dihydroxy-2(5H)-furanone;

5-[(3-(4-methoxyfur)-2-yl)phenyl]-5-cyclohexyl-3,4-dihydroxy-2(5H)-furanone;

5-[(4-(5-cyclohexylfur)-3-yl)phenyl]-5-methyl-3,4-dihydroxy-2(5H)-furanone;

5-[(3-(2-trifluoromethylfur)-3-yl)phenyl]-5-methyl-3,4-dihydroxy-2(5H)-furanone; and 5-[(2-(5-chlorofur)-3-yl)phenyl]-5-methyl -3,4-dihydroxy-2(5H)-furanone.

As noted above, the phenyl group may be optionally substituted, with $X^1$ as hereinbefore defined. Examples include:

5-[(4-(5-methylfur)-2-yl)2-chlorophenyl]-3,4-dihydroxy-2(5H)-furanone;

5-[(4-(5-methylfur)-2-yl)3-methylphenyl]-5-methyl-3,4-dihydroxy-2(5H)-furanone;

5-[(4-(5-methylfur)-2-yl)2-trifluoromethylphenyl]-5-phenyl-3,4-dihydroxy-2(5H)-furanone;

5-[(4-(5-methylfur)-2-yl)3-fluorophenyl]-5-(4-nitrophenyl)-3,4-dihydroxy-2(5H)-furanone;

5-[(3-(4-chlorofur)-2-yl)2-methoxyphenyl]-5-methyl-3,4-dihydroxy-2(5H)-furanone;

5-[(4-(4-chlorofur)-2-yl)3-ethylphenyl]-5-phenyl-3,4-dihydroxy-2(5H)-furanone;

5-[(3-(4-methoxyfur)-2-yl)5-chlorophenyl]-5-cyclohexyl-3,4-dihydroxy-2(5H)-furanone;

5-[(4-(5-cyclohexylfur)-3-yl)3-bromophenyl]-5-methyl-3,4-dihydroxy-2(5H)-furanone;

5-[(3-(2-trifluoromethylfur)-3-yl)2-fluorophenyl]-5-methyl-3,4-dihydroxy-2(5H)-furanone; and 5-[(2-(5-chlorofur)-3-yl)4-cyclohexylphenyl]-5-methyl-3,4-dihydroxy-2(5H)-furanone.

And in another example, Ar represents 2-pyridyl group as shown in formula V:

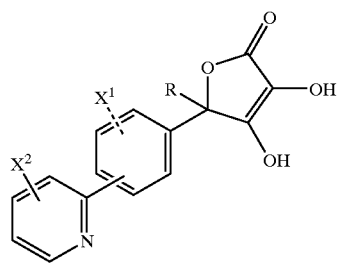

The pyridyl group may be attached at position 2 (as shown in formula V), 3 or 4. $X^1$ is as defined hereinabove. $X^2$ represents one or more halo, alkyl of one to eight carbon atoms, alkoxy of one to eight carbon atoms, cycloalkyl, nitro or trifluoromethyl groups. Non-limiting examples include 5-[(4-(5-methylpyrid)-2-yl)phenyl]-3,4-dihydroxy-2(5H)-furanone;

5-[(4-(3-methylpyrid)-2-yl)phenyl]-3,4-dihydroxy-2(5H)-furanone;

5-[(4-(4-methylpyrid)-2-yl)phenyl]-3,4-dihydroxy-2(5H)-furanone;

5-[(4-(4-methylpyrid)-3-yl)phenyl]-3,4-dihydroxy-2(5H)-furanone;

5-[(4-(5-methylpyrid)-3-yl)phenyl]-3,4-dihydroxy-2(5H)-furanone;

5-[(4-(2-methylpyrid)-3-yl)phenyl]-3,4-dihydroxy-2(5H)-furanone;

5-[(4-(5-methylpyrid)-2-yl)phenyl]-5-methyl-3,4-dihydroxy-2(5H)-furanone;

5-[(4-(5-methylpyrid)-2-yl)phenyl]-5-phenyl-3,4-dihydroxy-2(5H)-furanone;

5-[(4-(5-methylpyrid)-2-yl)phenyl]-5-(4-nitrophenyl)-3,4-dihydroxy-2(5H)-furanone;

5-[(3-(4-chloropyrid)-2-yl)phenyl]-5-methyl-3,4-dihydroxy-2(5H)-furanone;

5-[(4-(4-chloropyrid)-2-yl)phenyl]-5-phenyl-3,4-dihydroxy-2(5H)-furanone;

5-[(3-(4-methoxypyrid)-2-yl)phenyl]-5-cyclohexyl-3,4-dihydroxy-2(5H)-furanone;

5-[(4-(5-cyclohexylpyrid)-3-yl)phenyl]-5-methyl-3,4-dihydroxy-2(5H )-furanone;

5-[(3-(2-trifluoromethylpyrid)-3-yl)phenyl]-5-methyl-3,4-dihydroxy-2(5H)-furanone; and 5-[(2-(5-chloropyrid)-3-yl)phenyl]-5-methyl-3,4-dihydroxy-2(5H)-furanone.

As noted above, the phenyl group may be optionally substituted, with $X^1$ as hereinbefore defined. Examples include:

5-[(4-(5-methylpyrid)-2-yl)2-chlorophenyl]-3,4-dihydroxy-2(5H)-furanone;

5-[(4-(3-methylpyrid)-2-yl)3-methylphenyl]-3,4-dihydroxy-2(5H)-furanone;

5-[(4-(4-methylpyrid)-2-yl)2-trifluoromethylphenyl]-3,4-dihydroxy-2(5H)-furanone;

5-[(4-(4-methylpyrid)-3-yl)3-fluorophenyl]-3,4-dihydroxy-2(5H)-furanone;

5-[(4-(5-methylpyrid)-3-yl)2-methoxyphenyl]-3,4-dihydroxy-2(5H)-furanone;

following steps (a), (b), and (c) was used to prepare examples of compounds of the present invention.

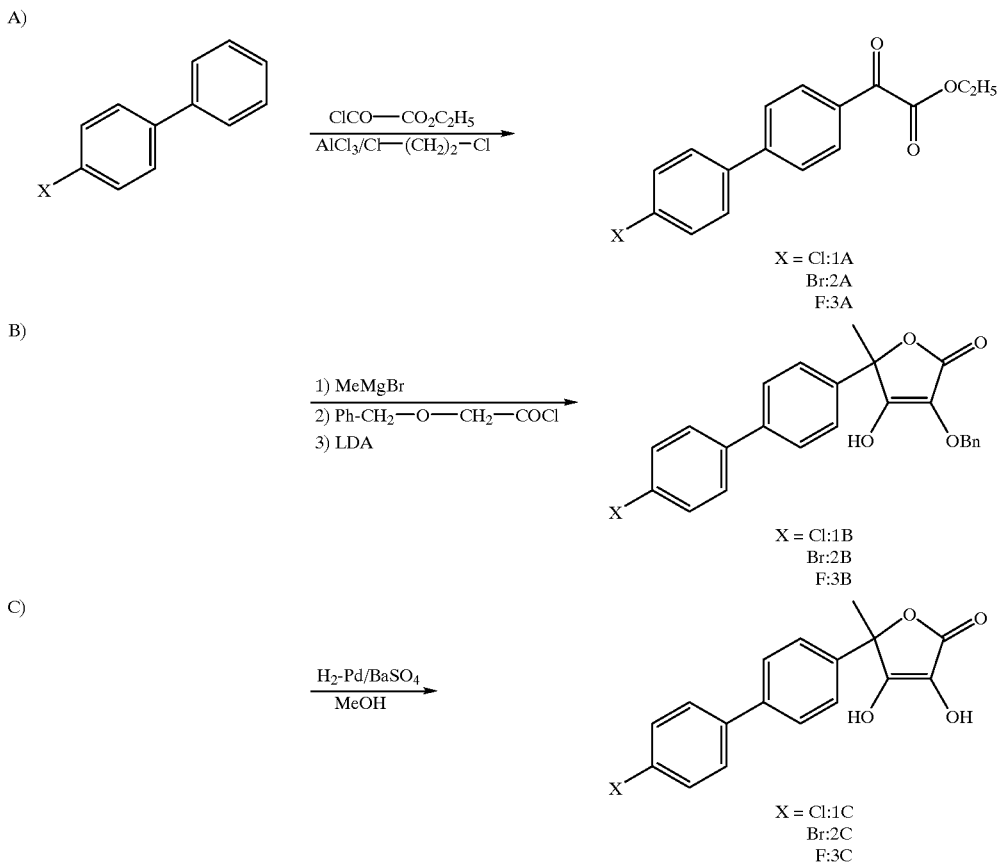

5-[(4-(2-methylpyrid)-3-yl)3-ethylphenyl]-3,4-dihydroxy-2(5H)-furanone;

5-[(4-(5-methylpyrid)-2-yl)5-chlorophenyl]-5-methyl-3,4-dihydroxy-2(5H)-furanone;

5-[(4-(5-methylpyrid)-2-yl)3-bromophenyl]-5-phenyl-3,4-dihydroxy-2(5H)-furanone;

5-[(4-(5-methylpyrid)-2-yl)2-cyclohexylphenyl]-5-(4-nitrophenyl)-3,4-dihydroxy-2(5H)-furanone;

5-[(3-(4-chloropyrid)-2-yl)2-fluorophenyl]-5-methyl-3,4-dihydroxy-2(5H)-furanone;

5-[(4-(4-chloropyrid)-2-yl)2-fluorophenyl]-5-phenyl-3,4-dihydroxy-2(5H)-furanone;

5-[(3-(4-methoxypyrid)-2-yl)5-trifluoromethylphenyl]-5-cyclohexyl-3,4-dihydroxy-2(5H)-furanone;

5-[(4-(5-cyclohexylpyrid)-3-yl)2-fluorophenyl]-5-methyl-3,4-dihydroxy-2(5H)-furanone;

5-[(3-(2-trifluoromethylpyrid)-3-yl)5-trifluoromethylphenyl]-5-methyl-3,4-dihydroxy-2(5H)-furanone; and 5-[(2-(5-chloropyrid)-3-yl)4-cyclohexylphenyl]-5-methyl-3,4-dihydroxy-2(5H)-furanone.

The disclosure of co-pending application Ser. No. 08/915,099, described the synthesis of unsubstituted 5-biphenyl compounds related to those described herein. Similar methods were used to prepared the present compounds. By way of non-limiting example, the following reaction scheme Alternatively, the optionally substituted ethyl 4-bromophenylglyoxylate compounds VI, below, can be prepared by Friedel-Crafts reaction between ethyl oxalyl chloride and a commercially available substituted bromobenzene. Reaction of the substituted ethyl 4-bromophenylglyoxylate with a Grignard reagent, acylation with benzyloxyacetyl chloride and cyclization with LDA provides tetronic acids VII. Suzuki reaction (N. Miyaura and A. Suzuki, Palladium-Catalysed Cross-Coupling Reactions of Organoboron Compounds: Chem. Rev., 1995, 95, 2457.) of the 4-bromophenyltetronic acid VII with an aryl boronic acid and subsequent removal of the benzyl protecting group provides compounds of formula I.

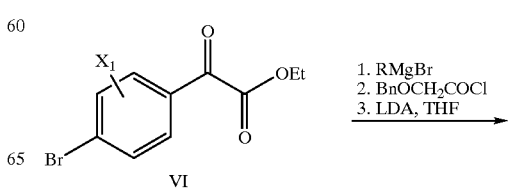

-continued

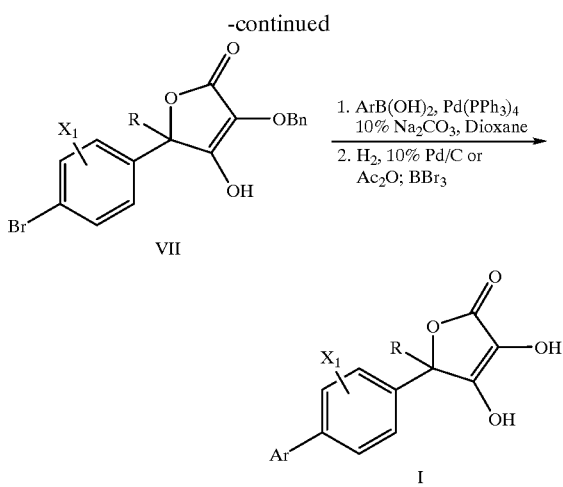

The Examples below describe the particular reactions to prepare the instant compounds. The starting materials utilized in the synthesis of the compounds herein are known in the art and/or are preparable by methods described herein. Where the pure optical isomers of these compounds are desired, numerous methods exist for the manufacture of optically active and optically pure derivatives of the necessary starting materials. Also, a wide range of chiral bases can be used to starting materials and intermediate products. Partial separation of enantiomers can typically be accomplished with optically active solvents such as (−)-menthone, (−)-menthyl acetate and (+)-limonene. Anion-exchange chromatography using a chiral stationary phase constructed of 1-p-nitrophenyl-2-amino-1,3-propanediol, or chromatography through starch successfully separates mandelic acid enantiomers.

The invention also provides for pharmaceutical compositions comprising the compounds of formula I above, as well as their physiologically acceptable salts (such as, for example, $Na^+$, $K^+$, $NH_4^+$).

Pharmaceutical compositions comprise a compound of the invention and a pharmaceutically acceptable carrier. Such pharmaceutical compositions may be for administration for injection, or for oral, pulmonary, nasal or other forms of administration. In general, comprehended by the invention are pharmaceutical compositions comprising effective amounts of a compound of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present compounds. See, e.g., Remington's Pharmaceutical Sciences, 18th Ed. (1990, Mack Publishing Co., Easton, Pa. 18042) pages 1435–1712 which are herein incorporated by reference. The compositions may be prepared in liquid form, or may be in dried powder, such as lyophilized form.

For oral delivery, contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: Modern Pharmaceutics Edited by G. S. Banker and C. T. Rhodes Chapter 10, 1979, herein incorporated by reference. In general, the formulation will include the component or components (or chemically modified forms thereof) and inert ingredients which allow for protection against the stomach environment, and release of the biologically active material in the intestine.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Controlled release oral formulation may be desirable. The drug could be incorporated into an inert matrix which permits release by either diffusion or leaching mechanisms, e.g., gums. Slowly degenerating matrices may also be incorporated into the formulation. Some enteric coatings also have a delayed release effect.

Another form of a controlled release of this therapeutic is by a method based on the Oros therapeutic system (Alza Corp.), i.e. the drug is enclosed in a semipermeable membrane which allows water to enter and push drug out through a single small opening due to osmotic effects. Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

For all of the above molecules, as further studies are conducted, information will emerge regarding appropriate dosage levels for treatment of various conditions in various patients, and the ordinary skilled worker, considering the therapeutic context, age and general health of the recipient, will be able to ascertain proper dosing. The dosing amount and schedule may vary, depending on the circulation half-life, and the formulation used. For example, a dose of 1 mg up to about 500 mg per day is embraced herein.

The compounds of the invention have antioxidant, anti-inflammatory, and antiaggregatory properties. As such, they are useful in the treatment of a variety of inflammatory and related disorders. As noted in the co-pending application Ser. No. 08/915,099, such compounds demonstrate the ability to inhibit the action of various inflammatory cytokines make them useful in a wide variety of therapeutic methods. Specifically, their ability to mediate or inhibit the actions of TNF-α makes these compounds useful in the treatment of various invasive diseases, infections, and inflammatory states. Particularly important is the inhibition of the large amount of TNF produced during serious bacterial infections, which can trigger a state of shock and tissue injury (septic shock syndrome).

A further important use of the compounds herein to inhibit the TNF which is known to mediate cachexia produced during chronic disease states. Thus, these compounds are particularly useful in adjunctive therapy for AIDS and cancer patients to reduce and/or ameliorate the consequences of cachexia produced during these chronic disease states.

A further specific method of treatment for which the compounds of the instant invention are particularly useful is in the treatment of rheumatoid arthritis wherein increased amounts of the inflammatory cytokines, TNF-α and IL-1 are present. By virtue of their ability to mediate and/or inhibit the action of these cytokines, inflammation and the severity of the disease state can be reduced or eliminated.

The compounds of the instant invention can also be utilized in the treatment of multiple sclerosis (MS), Crohn's disease and ulcerative colitis by inhibiting and the activity of the inflammatory cytokines which underlie these disease states.

Compounds useful for the aforementioned purposes are as described hereinabove. In one embodiment, the pathology comprises an acute or chronic inflammatory disorder, such as by way of non-limiting example, asthma, rheumatoid arthritis, inflammatory bowel disease, or acute respiratory distress syndrome.

In another embodiment, the pathology comprises neurodegenerative disorders, such as but not limited to Alzheimer disease, Parkinson disease, amyotrophic lateral sclerosis, traumatic brain injury or multiple sclerosis. In a further embodiment, the pathology comprises cardiovascular disease, such as atherosclerosis. In yet a further embodiment, the pathology comprises a viral disease, such as but not limited to AIDS. In still yet a further embodiment, the pathology comprises a skin disease, such as psoriasis, sunburn, and premature aging of the skin.. In yet another embodiment, the pathology comprises an eye disease, such as but not limited to glaucoma, cataract, senile macular degeneration, inflammatory eye conditions, trauma, post-traumatic eye disorders, diabetic retinopathy, and eye infections.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Preparation of 5-(4-chlorobiphenyl)-5-methyl-3,4-dihydroxy furan-2-one: (1C)

For this and all experiments described herein, reagents and solvents were of commercial quality and were used as received. Anhydrous THF was obtained, prior to use, by distillation from sodium diphenyl ketyl. Reactions were carried out under $N_2$ with the use of standard procedures for the exclusion of moisture unless otherwise noted. $^1H$ and $^{13}C$ spectra were recorded on a Varian 200 MHz Spectrometer; chemical shifts are reported related to internal $SiMe_4$ and J values are given in Hz. Melting points are measured on a Gallenkamp apparatus and are uncorrected. TLC was performed on silica gel (Macherey Nagel) developed using cyclohexane/ethyl acetate mixtures as described in the text. Mass spectra were recorded on a Nermay R10-10B instrument. The ionization mode used is either electron impact (El) at 70 electron volts or chemical ionization (CI) in 2-methylpropane.

5-(4-chlorobiphenyl)-5-methyl-3,4-dihydroxy furan-2-one was prepared following the reaction scheme described above, wherein $X^2=Cl$.

A) Preparation of ethyl 4-chlorobiphenyl glyoxylate 1A (general procedure for Friedel-Craft acylation): In a 2000 ml three-necked flask equipped with a thermometer and a mechanical stirrer was placed 4-chlorobiphenyl (49.5 g; 262 mmol; 1 eq.) and ethyl oxalyl chloride (47.03 g; 344 mmol; 1.3 eq.) in dichloroethane (195 ml). To this precooled solution (15° C.) was added portionwise over 30 min aluminium chloride (69.25 g; 518 mmol; 2 eq.). During addition, due to the reaction exothermicity, internal temperature should be kept below 20° C. The reaction progress was monitored by TLC (cyclohexane/ethyl acetate 4/1).

After 30 min stirring at 20° C., the red mixture was quenched by 10% HCl solution (480 ml). The organic phase was decanted and the acidic aqueous layer extracted twice with dichloromethane (100 ml). To remove traces of aluminium salts from the collected organic phases, silica gel (200 g) was then added and vigorous stirring maintained during 30 min. After filtration over a celite pad, the filtrate was washed with saturated $NaHCO_3$ aqueous solution (2×200 ml) and water (2×100 ml). After evaporation of the solvent, the crude semi-solid residue was then recrystallized in cyclohexane to provide after filtration and drying, ethyl 4-chlorobiphenyl glyoxylate 1A (63.8 g; 85%) as white needles. $^1H$ NMR ($CDCl_3$) δ:1.42 (t, 3H, 7.1); 4.45 (q, 2H, 7.1); 7.41 (d, 2H, 8.1); 7.56 (d, 2H, 8.1); 7.63 (d, 2H, 8.2); 8.04 (d, 2H, 8.2).

B) Preparation of 5-(4-chlorobiphenyl)-5-methyl-3-benzyloxy-4-hydroxyfuran-2-one (1B in scheme above) (general procedure for Dieckman cyclization): In a 2000 ml three-necked flask equipped with mechanical stirrer, thermometer and dropping funnel, was placed ketoester 1A (56.8 g; 196 mmol; 1 eq.) in THF (650 ml). The flask was immersed in a ice-acetone bath and MeMgBr (3.0 M in ether; 70 ml; 210 mmol; 1.05 eq.) was dropped into the cooled solution (−10° C.) over 15 min. After being stirred for 30 min at −10° C., benzyloxyacetyl chloride (39.5 g; 215 mmol; 1.1 eq.) was added. The reaction mixture allowed to warm to room temperature, was stirred for 2 h and cooled again to −10° C. before dropwise addition of LDA (2M sol. in THF; 128 ml; 256 mmol; 1.3 eq.). Stirring at −10° C. was maintained for 1 h. After being quenched with saturated $NH_4Cl$ solution (100 ml), the mixture was diluted with water (100 ml), acidified to pH=1 with 50% aqueous HCl (120 ml) and then extracted with AcOEt (3=100 ml).

The combined extracts were washed successively with water (2×100 ml), brine (100 ml) and dried over $MgSO_4$. After filtration, the mixture was evaporated to dryness and the crude residue triturated with a mixture of AcOEt/Cyclohexane (1/10; 120 ml). The finely dispersed solid was filtered, washed with cyclohexane (20 ml) and dried in a vacuum oven to provide without further purification, 5-(4-chlorobiphenyl)-5-methyl -3-benzyloxy-4-hydroxy furan-2-one 1B (21 g; 26%) as a white solid. $^1H$ NMR ($CDCl_3$) δ:1.76 (s, 3H); 5.12 (s, 2H); 7.30–7.60 (m, 13H).

C) Preparation of 5-(4-chlorobiphenyl)-5-methyl-3,4-dihydroxy furan-2-one 1C: (general procedure for debenzylation) To a solution of benzyl ether 1B (21 g; 51.17 mmol) in MeOH (200 ml) was added a catalytic amount of 10% Pd/BaSO$_4$ (2.10 g ). The resulting suspension was then hydrogenated at room temperature (2 bars) under vigorous stirring for 1 hour. Reaction progress was carefully monitored by TLC (eluant: cyclohexane/ethyl acetate : 2/1). After filtration of palladium catalyst, MeOH was evaporated under reduced pressure. The solid residue, triturated with cyclohexane/ethyl acetate (4/1), was filtered, rinsed with the same solvent mixture and finally dried to provide 5-(4-chlorobiphenyl)-5-methyl-3,4-dihydroxy furan-2-one 1C (13.4 g; 82%). $^1$H NMR (Acetone) δ:1.85 (s, 3H); 7.35–7.80 (m, 8H).

EXAMPLE 2

Preparation of 5-(4-bromobiphenyl)-5-methyl-3,4-dihydroxy furan-2-one: (2C)

A) Preparation of ethyl 4-bromobiphenyl glyoxylate 2A: According to the general procedure described for compound 1A, ethyl 4-bromobiphenyl glyoxylate 2A (13.8 g; 96%) was obtained as a white solid, starting from 4-bromobiphenyl (10 g; 43 mmol), ethyloxalyl chloride (6.61 g; 55.7 mmol) and aluminium chloride ( 11.4 g; 85.4 mmol) in dichloroethane (30 ml). $^1$H NMR (CDCl$_3$) δ:1.41 (t, 3H, 7.2); 4.44 (q, 2H, 7.2); 7.48 (d, 2H, 8.3); 7.59 (d, 2H, 8.3); 7.66 (d, 2H, 8.2); 8.08 (d, 2H, 8.2).

B) Preparation of 5-(4-bromobiphenyl)-5-methyl-3-benzyloxy-4-hydroxy furan-2-one 2B: According to the general procedure described for compound 1B, compound 2B (3.6 g; 19.5%) was obtained as a white solid after trituration from a mixture of cyclohexane/ethyl acetate (10/1), starting from ketoester 2A (13.5 g, 40.4 mmol), MeMgBr (3.0 M in ether ;14.2 ml, 42.6 mmol) in THF (120 ml), benzyloxyacetyl chloride (8.22 g, 44.5 mmol) and LDA (2.0 M in THF; 28.3 ml; 56.7 mmol).

$^1$H NMR (CDCl$_3$) δ:1.78 (s, 3H); 5.10 (s, 2H); 7.30–7.55 (m, 13H).

C) Preparation of 5-(4-bromobiphenyl)-5-methyl-3,4-dihydroxy furan-2-one 2C: According to the general procedure described for compound IC, compound 2C (1.4 g; 82%) was obtained as a white solid after crystallization in a mixture of EtOH/H$_2$O (1/1; 7 ml), starting from benzyl ether 2B (2.16 g, 4.9 mM), 10% Pd/BaSO$_4$ (0.21 g) in MeOH (50 ml).

$^1$H NMR (Acetone) δ:1.86 (s, 3H); 7.30–7.50 (m, 2H); 7.55–7.70 (m, 6H). $^{13}$C NMR (Acetone) δ:24.3; 81.2; 118.0; 126.7; 127.7; 128.3; 129.7; 132.8; 139.9; 141.1; 141.7; 157.2; 159.5. CIMS:247 (16); 282 (12); 283 (100); MH$^+$361/ 363 (4/).

EXAMPLE 3

Preparation of 5-(4-fluorobiphenyl)-5-methyl-3,4-dihydroxy furan-2-one (3C)

A) Preparation of ethyl 4-fluorobiphenyl glyoxylate 3A : According to the general procedure described for compound 1A, ethyl 4-fluorobiphenyl glyoxylate 3A (6.2 g; 98%) was obtained as a white solid, starting from 4-fluorobiphenyl (4.0 g; 23.2 mmol), ethyloxalyl chloride (4.1 g; 30 mmol) and aluminium chloride ( 6.2 g; 46.4 mmol) in dichloroethane (30 ml).

$^1$H NMR (CDCl$_3$) δ:1.42 (t, 3H, 7.2); 4.45 (q, 2H, 7.2); 7.15 (t, 2H); 7.60 (dd, 2H, 8.0, 6.2); 7.66 (d, 2H, 8.1); 8.07 (d, 2H, 8.1).

B) Preparation of 5-(4-fluorobiphenyl)-5-methyl -3-benzyloxy-4-hydroxy furan-2-one 3B: According to the general procedure described for compound 1B, compound 3B (1.25 g; 13.6%) was obtained as a white solid after trituration from a mixture of cyclohexane/ethyl acetate (10/ 1) starting from ketoester 3A (6.40 g; 23.4 mmol), MeMgBr (3.0 M in ether; 8.24 ml, 24.7 mmol), in THF (75 ml), benzyloxyacetyl chloride (4.99 g, 27 mmol), LDA (2.0 M in THF; 16.4 ml; 32.8 mmol). $^1$H NMR (CDCl$_3$) δ:1.78 (s, 3H); 5.09 (s, 2H); 7.10 (m, 2H); 7.30–7.52 (m, 11H).

C) Preparation of 5-(4-fluorobiphenyl)-5-methyl-3,4-dihydroxy furan-2-one 3C According to the general procedure described for compound 1C, compound 3C (0.80 g; 84%) was obtained as a white solid after crystallization in a mixture of EtOH/H$_2$O (1/3; 20 ml), starting from benzyl ether 3B (1.25 g, 3.2 mmol), 10% Pd/BaSO$_4$ (0.12 g) in MeOH (25 ml).

$^1$H NMR (Acetone) δ:1.85 (s, 3H); 7.21 (m, 2H); 7.52–7.85 (m, 6H).

$^{13}$C NMR(Acetone) δ:24.2; 81.5; 116.1; 116.6; 117.9; 126.7; 127.6; 129.5; 129.7; 139.9; 140.6; 157.5;161.2; 166.0; 169.6. CIMS 170 (44); 183 (23); 199 (100); 241 (39); 226 (24); 254 (42); 282 (26); M$^+$300 (72).

EXAMPLE 4

Preparation of Additional Compounds

Following the aforementioned procedures, the following compounds are prepared:

5-[(4'-fluoro-1,1'-biphenyl)-4-yl]-3,4-dihydroxy-2(5H)-furanone;

5-[(4'-fluoro-1,1'-biphenyl)-4-yl]-5-methyl-3,4-dihydroxy-2(5H)-furanone;

5-[(4'-fluoro-1,1'-biphenyl)-4-yl]-5-phenyl-3,4-dihydroxy-2(5H)-furanone;

5-[(4'-fluoro-1,1'-biphenyl)-4-yl]-5-cyclohexyl-3,4-dihydroxy-2(5H)-furanone;

5-[(4'-fluoro-1,1'-biphenyl)-4-yl]-5-(4-nitrophenyl)-3,4-dihydroxy-2(5H)-furanone;

5-[(4'-bromo-1,1'-biphenyl)-4-yl]-5-methyl-3,4-dihydroxy-2(5H)-furanone;

5-[(4'-chloro-1,1'-biphenyl)-4-yl]-5-methyl-3,4-dihydroxy-2(5H)-furanone;

5-[(2',4'-dichloro-1,1'-biphenyl)-4-yl]-3,4-dihydroxy-2(5H)-furanone;

5-[(2',4'-dichloro-1,1'-biphenyl)-4-yl]-5-methyl-3,4-dihydroxy-2(5H)-furanone;

5-[(4'-chloro-1,1'-biphenyl)-4-yl]-5-phenyl-3,4-dihydroxy-2(5H)-furanone;

5-[(4'-trifluoromethyl-1,1'-biphenyl)-4-yl]-3,4-dihydroxy-2(5H)-furanone;

5-[(4'-trifluoromethyl-1,1'-biphenyl)-4-yl]-5-methyl-3,4-dihydroxy-2(5H)-furanone;

5-[(4'-trifluoromethyl-1,1'-biphenyl-4-yl]-5-phenyl-3,4-dihydroxy-2(5H)-furanone;

5-[(4'-trifluoromethyl-1,1'-biphenyl)-4-yl]-5-cyclohexyl-3,4-dihydroxy-2(5H )-furanone;

5-[(4'-trifluoromethyl-1,1'-biphenyl)-4-yl]-5-(4-methylphenyl)-3,4-dihydroxy-2(5H)-furanone;

5-[(4'-trifluoromethyl-1,1'-biphenyl)-4-yl]-5-(4-methoxyphenyl)-3,4-dihydroxy-2(5H)-furanone;

5-[(4'-nitro-1,1'-biphenyl)-4-yl]-3,4-dihydroxy-2(5H)-furanone;

5-[(4'-nitro-1,1'-biphenyl)-4-yl]-5-ethyl-3,4-dihydroxy-2(5H)-furanone;

5-[(4'-nitro-1,1'-biphenyl)-4-yl]-5-phenyl-3,4-dihydroxy-2(5H)-furanone;

5-[(4'-nitro-1,1'-biphenyl)-4-yl]-5-cyclohexyl-3,4-dihydroxy-2(5H)-furanone;

5-[(4'-nitro-1,1'-biphenyl)-4-yl]-5-(4-trifluoromethylphenyl)-3,4-dihydroxy-2(5H)-furanone;
5-[(4'-cyclohexyl-1,1'-biphenyl)-4-yl]-3,4-dihydroxy-2(5H)-furanone;
5-[(4'-cyclohexyl-1,1'-biphenyl)-4-yl]-5-methyl-3,4-dihydroxy-2(5H)-furanone;
5-[(4'-cyclohexyl-1,1'-biphenyl)-4-yl]-5-phenyl-3,4-dihydroxy-2(5H)-furanone;
5-[(4'-cyclohexyl-1,1'-biphenyl)-4-yl]-5-cyclopentyl-3,4-dihydroxy-2(5H)-furanone;
5-[(4'-cyclohexyl-1,1'-biphenyl)-4-yl]-5-(4-ethoxyphenyl)-3,4-dihydroxy-2(5H)-furanone;
5-[(4'-ethyl-1,1'-biphenyl)-4-yl]-3,4-dihydroxy-2(5H)-furanone;
5-[(4'-methyl-1,1'-biphenyl)-4-yl]-5-methyl-3,4-dihydroxy-2(5H)-furanone;
5-[(2',4'-dimethyl-1,1'-biphenyl)-4-yl]-3,4-dihydroxy-2(5H)-furanone;
5-[(2',4'-dimethyl-1,1'-biphenyl)-4-yl]-5-methyl-3,4-dihydroxy-2(5H)-furanone;
5-[(2',4'-dimethyl-1,1'-biphenyl)-4-yl]-5-phenyl-3,4-dihydroxy-2(5H)-furanone;
5-[(4'-methyl-1,1'-biphenyl)-4-yl]-5-(2-chloropropyl)-3,4-dihydroxy-2(5H)-furanone;
5-[(4'-methyl-1,1'-biphenyl)-4-yl]-5-cyclopropyl-3,4-dihydroxy-2(5H)-furanone;
5-[(4'-methyl-1,1'-biphenyl)-4-yl]-5-phenyl-3,4-dihydroxy-2(5H)-furanone;
5-[(4'-ethyl-1,1'-biphenyl)-4-yl]-5-(4-nitrophenyl)-3,4-dihydroxy-2(5H)-furanone;
5-[(4'-methoxy-1,1'-biphenyl)-4-yl]-3,4-dihydroxy-2(5H)-furanone;
5-[(4'-methoxy-1,1'-biphenyl)-4-yl]-5-methyl-3,4-dihydroxy-2(5H)-furanone;
5-[(4'-methoxy-1,1'-biphenyl)-4-yl]-5-chloromethyl-3,4-dihydroxy-2(5H)-furanone;
5-[(4'-methoxy-1,1'-biphenyl)-4-yl]-5-phenyl-3,4-dihydroxy-2(5H)-furanone;
5-[(3,4'-dichloro-1,1'-biphenyl)-4-yl]-3,4-dihydroxy-2(5H)-furanone;
5-[(3,4'-dichloro-1,1'-biphenyl)-4-yl]-5-methyl-3,4-dihydroxy-2(5H)-furanone;
5-[(3,4'-dichloro-1,1'-biphenyl)-4-yl]-5-phenyl-3,4-dihydroxy-2(5H)-furanone;
5-[(3,4'-dichloro-1,1'-biphenyl)-4-yl]-5-cyclohexyl-3,4-dihydroxy-2(5H)-furanone;
5-[(3,4'-dichloro-1,1'-biphenyl)-4-yl]-5-(4-nitrophenyl)-3,4-dihydroxy-2(5H)-furanone;
5-[(3,4'-dimethyl-1,1'-biphenyl)-4-yl]-3,4-dihydroxy-2(5H)-furanone;
5-[(3,4'-dimethyl-1,1'-biphenyl)-4-yl]-5-methyl-3,4-dihydroxy-2(5H)-furanone;
5-[(3,4'-dimethyl-1,1'-biphenyl)-4-yl]-5-phenyl-3,4-dihydroxy-2(5H)-furanone;
5-[(3,4'-dimethyl-1,1'-biphenyl)-4-yl]-5-cyclohexyl-3,4-dihydroxy-2(5H)-furanone
5-[(3,4'-dimethyl-1,1'-biphenyl)-4-yl]-5-4-nitrophenyl)-3,4-dihydroxy-2(5H)-furanone;
5-[(3-chloro-4'-methyl-1,1'-biphenyl)-4-yl]-3,4-dihydroxy-2(5H)-furanone;
5-[(3-chloro-4'-methyl-1,1'-biphenyl)-4-yl]-5-methyl-3,4-dihydroxy-2(5H)-furanone;
5-[(3-chloro-4'-methyl-1,1'-biphenyl)-4-yl]-5-phenyl-3,4-dihydroxy-2(5H)-furanone;
5-[(3-chloro-4'-methyl-1,1'-biphenyl)-4-yl]-5-cyclohexyl-3,4-dihydroxy-2(5H)-furanone;
5-[(3-chloro-4'-methyl-1,1'-biphenyl)-4-yl]-5-(4-nitrophenyl)-3,4-dihydroxy-2(5H)-furanone
5-[4-(1-(2-chloronaphthyl))phenyl]-3,4-dihydroxy-2(5H)-furanone;
5-[4-(1-(2,5-dichloronaphthyl))phenyl]-3,4-dihydroxy-2(5H)-furanone;
5-[4-(1-(2-chloronaphthyl))phenyl]-5-methyl-3,4-dihydroxy-2(5H)-furanone;
5-[4-(2-(6-methylnaphthyl))phenyl]-5-methyl-3,4-dihydroxy-2(5H)-furanone;
5-[4-(1-(3-methylnaphthyl))phenyl]-5-methyl-3,4-dihydroxy-2(5H)-furanone;
5-[4-(2-(1-methylnaphthyl))phenyl]-5-methyl-3,4-dihydroxy-2(5H)-furanone;
5-[4-(1-(2-chloronaphthyl))phenyl]-5-phenyl-3,4-dihydroxy-2(5H)-furanone;
5-[4-(1-(2-chloronaphthyl))phenyl]-5-cyclohexyl-3,4-dihydroxy-2(5H)-furanone;
5-[4-(1-(2-chloronaphthyl))phenyl]-5-(4-toluyl)-3,4-dihydroxy-2(5H)-furanone;
5-[4-(1-(3-methylnaphthyl))phenyl]-5-(4-anisoyl)-3,4-dihydroxy-2(5H)-furanone;
5-[4-(1-(3-methylnaphthyl))phenyl]-5-ethyl-3,4-dihydroxy-2(5H)-furanone;
5-[4-(1-(3-methylnaphthyl))phenyl]-5-nitrophenyl-3,4-dihydroxy-2(5H)-furanone;
5-[4-(1-(3-methylnaphthyl))phenyl]-5-(4-chlorophenyl)-3,4-dihydroxy-2(5H)-furanone;
5-[(4-(5-methylthien)-2-yl)phenyl]-3,4-dihydroxy-2(5H)-furanone;
5-[(4-(5-methylthien)-2-yl)phenyl]-5-methyl-3,4-dihydroxy-2(5H)-furanone;
5-[(4-(5-methylthien)-2-yl)phenyl]-5-phenyl-3,4-dihydroxy-2(5H)-furanone;
5-[(4-(5-methylthien)-2-yl)phenyl]-5-(4-nitrophenyl)-3,4-dihydroxy-2(5H)-furanone;
5-[(3-(4-chlorothien)-2-yl)phenyl]-5-methyl-3,4-dihydroxy-2(5H)-furanone;
5-[(4-(4-chlorothien)-2-yl)phenyl]-5-phenyl-3,4-dihydroxy-2(5H)-furanone;
5-[(3-(4-methoxythien)-2-yl)phenyl]-5-methyl-3,4-dihydroxy-2(5H)-furanone;
5-[(4-(5-cyclohexylthien)-3-yl)phenyl]-5-methyl-3,4-dihydroxy-2(5H)-furanone;
5-[(3-(2-trifluoromethylthien)-3-yl)phenyl]-5-methyl-3,4-dihydroxy-2(5H)-furanone;
5-[(2-(5-chlorothien)-3-yl)phenyl]-5-methyl-3,4-dihydroxy-2(5H)-furanone;
5-[(4-(5-methylthien)-2-yl)2-chlorophenyl]-3,4-dihydroxy-2(5H)-furanone;
5-[(4-(5-methylthien)-2-yl)3-methylphenyl]-5-methyl-3,4-dihydroxy-2(5H)-furanone;
5-[(4-(5-methylthien)-2-yl)2-trifluoromethylphenyl]-5-phenyl-3,4-dihydroxy-2(5H)-furanone;
5-[(4-(5-methylthien)-2-yl)3-fluorophenyl]-5-(4-nitrophenyl)-3,4-dihydroxy-2(5H)-furanone;
5-[(3-(4-chlorothien)-2-yl)2-methoxyphenyl]-5-methyl-3,4-dihydroxy-2(5H)-furanone;

5-[(4-(4-chlorothien)-2-yl)3-ethylphenyl]-5-phenyl-3,4-dihydroxy-2(5H)-furanone;
5-[(3-(4-methoxythien)-2-yl)5-chlorophenyl]-5-methyl-3,4-dihydroxy-2(5H)-furanone;
5-[(4-(5-cyclohexylthien)-3-yl)3-bromophenyl]-5-methyl-3,4-dihydroxy-2(5H)-furanone;
5-[(3-(2-trifluoromethylthien)-3-yl)2-fluorophenyl]-5-methyl-3,4-dihydroxy-2(5H)-furanone;
5-[(2-(5-chlorothien)-3-yl)4-cyclohexylphenyl]-5-methyl-3,4-dihydroxy-2(5H)-furanone;
5-[(4-(5-methylfur)-2-yl)phenyl]-3,4-dihydroxy-2(5H)-furanone;
5-[(4-(5-methylfur)-2-yl)phenyl]-5-methyl-3,4-dihydroxy-2(5H)-furanone;
5-[(4-(5-methylfur)-2-yl)phenyl]-5-phenyl-3,4-dihydroxy-2(5H)-furanone;
5-[(4-(5-methylfur)-2-yl)phenyl]-5-(4-nitrophenyl)-3,4-dihydroxy-2(5H)-furanone;
5-[(3-(4-chlorofur)-2-yl)phenyl]-5-methyl-3,4-dihydroxy-2(5H)-furanone;
5-[(4-(4-chlorofur)-2-yl)phenyl]-5-phenyl-3,4-dihydroxy-2(5H)-furanone;
5-[(3-(4-methoxyfur)-2-yl)phenyl]-5-cyclohexyl-3,4-dihydroxy-2(5H)-furanone;
5-[(4-(5-cyclohexylfur)-3-yl)phenyl]-5-methyl-3,4-dihydroxy-2(5H)-furanone;
5-[(3-(2-trifluoromethylfur)-3-yl)phenyl]-5-methyl-3,4-dihydroxy-2(5H)-furanone;
5-[(2-(5-chlorofur)-3-yl)phenyl]-5-methyl-3,4-dihydroxy-2(5H)-furanone;
5-[(4-(5-methylfur)-2-yl)2-chlorophenyl]-3,4-dihydroxy-2(5H)-furanone;
5-[(4-(5-methylfur)-2-yl)3-methylphenyl]-5-methyl-3,4-dihydroxy-2(5H)-furanone;
5-[(4-(5-methylfur)-2-yl)2-trifluoromethylphenyl]-5-phenyl-3,4-dihydroxy-2(5H)-furanone;
5-[(4-(5-methylfur)-2-yl)3-fluorophenyl]-5-(4-nitrophenyl)-3,4-dihydroxy-2(5H)-furanone;
5-[(3-(4-chlorofur)-2-yl)2-methoxyphenyl]-5-methyl-3,4-dihydroxy-2(5H)-furanone;
5-[(4-(4-chlorofur)-2-yl)3-ethylphenyl]-5-phenyl-3,4-dihydroxy-2(5H)-furanone;
5-[(3-(4-methoxyfur)-2-yl)5-chlorophenyl]-5-cyclohexyl-3,4-dihydroxy-2(5H)-furanone;
5-[(4-(5-cyclohexylfur)-3-yl)3-bromophenyl]-5-methyl-3,4-dihydroxy-2(5H)-furanone;
5-[(3-(2-trifluoromethylfur)-3-yl)2-fluorophenyl]-5-methyl-3,4-dihydroxy-2(5H)-furanone;
5-[(2-(5-chlorofur)-3-yl)4-cyclohexylphenyl]-5-methyl-3,4-dihydroxy-2(5H)-furanone;
5-[(4-(5-methylpyrid)-2-yl)phenyl]-3,4-dihydroxy-2(5H)-furanone;
5-[(4-(3-methylpyrid)-2-yl)phenyl]-3,4-dihydroxy-2(5H)-furanone;
5-[(4-(4-methylpyrid)-2-yl)phenyl]-3,4-dihydroxy-2(5H)-furanone;
5-[(4-(4-methylpyrid)-3-yl)phenyl]-3,4-dihydroxy-2(5H)-furanone;
5-[(4-(5-methylpyrid)-3-yl)phenyl]-3,4-dihydroxy-2(5H)-furanone;
5-[(4-(2-methylpyrid)-3-yl)phenyl]-3,4-dihydroxy-2(5H)-furanone;
5-[(4-(5-methylpyrid)-2-yl)phenyl]-5-methyl-3,4-dihydroxy-2(5H)-furanone;
5-[(4-(5-methylpyrid)-2-yl)phenyl]-5-phenyl-3,4-dihydroxy-2(5H)-furanone;
5-[(4-(5-methylpyrid)-2-yl)phenyl]-5-(4-nitrophenyl)-3,4-dihydroxy-2(5H)-furanone;
5-[(3-(4-chloropyrid)-2-yl)phenyl]-5-methyl-3,4-dihydroxy-2(5H)-furanone;
5-[(4-(4-chloropyrid)-2-yl)phenyl]-5-phenyl-3,4-dihydroxy-2(5H)-furanone;
5-[(3-(4-methoxypyrid)-2-yl)phenyl]-5-cyclohexyl-3,4-dihydroxy-2(5H)-furanone;
5-[(4-(5-cyclohexylpyrid)-3-yl)phenyl]-5-methyl-3,4-dihydroxy-2(5H)-furanone;
5-[(3-(2-trifluoromethylpyrid)-3-yl)phenyl]-5-methyl-3,4-dihydroxy-2(5H)-furanone;
5-[(2-(5-chloropyrid)-3-yl)phenyl]-5-methyl-3,4-dihydroxy-2(5H)-furanone;
5-[(4-(5-methylpyrid)-2-yl)2-chlorophenyl]-3,4-dihydroxy-2(5H)-furanone;
5-[(4-(3-methylpyrid)-2-yl)3-methylphenyl]-3,4-dihydroxy-2(5H)-furanone;
5-[(4-(4-methylpyrid)-2-yl)2-trifluoromethylphenyl]-3,4-dihydroxy-2(5H)-furanone;
5-[(4-(4-methylpyrid)-3-yl)3-fluorophenyl]-3,4-dihydroxy-2(5H)-furanone;
5-[(4-(5-methylpyrid)-3-yl)2-methoxyphenyl]-3,4-dihydroxy-2(5H)-furanone;
5-[(4-(2-methylpyrid)-3-yl)3-ethylphenyl]-3,4-dihydroxy-2(5H)-furanone;
5-[(4-(5-methylpyrid)-2-yl)5-chlorophenyl]-5-methyl-3,4-dihydroxy-2(5H)-furanone;
5-[(4-(5-methylpyrid)-2-yl)3-bromophenyl]-5-phenyl-3,4-dihydroxy-2(5H)-furanone;
5-[(4-(5-methylpyrid)-2-yl)2-cyclohexylphenyl]-5-(4-nitrophenyl)-3,4-dihydroxy-2(5H)-furanone;
5-[(3-(4-chloropyrid)-2-yl)2-fluorophenyl]-5-methyl-3,4-dihydroxy-2(5H)-furanone;
5-[(4-(4-chloropyrid)-2-yl)2-fluorophenyl]-5-phenyl-3,4-dihydroxy-2(5H)-furanone;
5-[(3-(4-methoxypyrid)-2-yl)5-trifluoromethylphenyl]-5-cyclohexyl-3,4-dihydroxy-2(5H)-furanone;
5-[(4-(5-cyclohexylpyrid)-3-yl)2-fluorophenyl]-5-methyl-3,4-dihydroxy-2(5H)-furanone;
5-[(3-(2-trifluoromethylpyrid)-3-yl)5-trifluoromethylphenyl]-5-methyl-3,4-dihydroxy-2(5H)-furanone; and
5-[(2-(5-chloropyrid)-3-yl)4-cyclohexylphenyl]-5-methyl-3,4-dihydroxy-2(5H)-furanone.

EXAMPLE 5

Inhibition Of LPS-induced E-selectin Expression By Endothelial Cells

It has been shown that the initial phase of inflammation is mediated by adhesion molecules such as E-selectin (see Albeda S. M. et al., FASEB Journal, 8: 504–512, 1994). Human endothelial cells are grown at 37° C. in multi-well plates under a water-saturated atmosphere constituted of a gaseous mixture of 95% air and 5% $CO_2$. Their culture medium is constituted by a medium M199 pH=7.4 contain ing 20% foetal calf serum, 2 mM L-glutamine, 100 U/ml penicillin, 100 μg/ml streptomycin and 1% by volume of a medium supplement containing heparin and a growth factor for these cells. When the cells are close to confluence, they are incubated for eighteen hours in the presence or in the absence of one of the following compounds: racemic 5-[(4'-chloro-1,1'-biphenyl)-4-yl]-5-methyl-3,4-dihydroxy-2(5H)-furanone; racemic 5-[(4'-bromo-1,1'-biphenyl)-4-yl]-5-methyl-3,4-dihydroxy-2(5H)-furanone; racemic 5-[(4'-fluoro-1,1'-biphenyl)-4-yl]-5-methyl-3,4-dihydroxy-2(5H)-furanone; and 5-(1,1'-biphenyl-4-yl)-5-methyl-3,4-dihydroxy-2(5H)- furanone. Each one of these compounds is incorporated at 100 μM in the culture medium. After the removal of the culture medium, the cells are incubated in the presence or in the absence (control) of LPS, at 50 ng/ml, in the same culture medium as before. In the case of cells pre-treated with a compound, the medium further contains the same compound at 100 μM. After six hours of incubation, the cells are washed with PBS buffer and they are fixed with 2% formaldehyde in the same buffer. The E-selectin expression on the cells is measured by an ELISA determination by successively incubating the cells in the presence of a mouse monoclonal antibody anti-E-selectin and a rabbit anti-mouse antibody labelled with alkaline phosphatase. The quantification is carried out upon the addition of paranitrophenyl phosphate whose hydrolysis is followed at 405 nm.

The results obtained are given in Table 1 below. They are expressed as percentages of inhibition of the LPS-induced expression of E-selectin.

TABLE 1

| Compound | E-selectin expression % inhibition (Mean ± SD) | (n) |
|---|---|---|
| racemic 5-[(4'-chloro-1,1'-biphenyl)-4-yl]-5-methyl-3,4-dihydroxy-2(5H)-furanone | 73 ± 24.6 | 12 |
| racemic 5-[(4'-bromo-1,1'-biphenyl)-4-yl]-5-methyl-3,4-dihydroxy-2(5H)-furanone | 92 ± 5.1 | 5 |
| racemic 5-[(4'-fluoro-1,1'-biphenyl)-4-yl]-5-methyl-3,4-dihydroxy-2(5H)-furanone | 96 ± 3.4 | 5 |
| 5-(1,1'-biphenyl-4-yl)-5-methyl-3,4-dihydroxy-2(5H)-furanone | 62 ± 27.3 | 10 |

These results show that racemic 5-[(4'-chloro-1,1'-biphenyl)-4-yl]-5-methyl-3,4-dihydroxy-2(5H)-furanone, racemic 5-[(4'-bromo-1,1'-biphenyl)-4-yl]-5-methyl-3,4-dihydroxy-2(5H)-furanone; racemic 5-[(4'-fluoro-1,1'-biphenyl)4-yl]-5-methyl-3,4-dihydroxy-2(5H)-furanone inhibit the LPS-induced expression of E-selectin.

The present invention is not to be limited in scope by the specific embodiments describe herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed is:

1. A racemic or optically active compound of the formula I

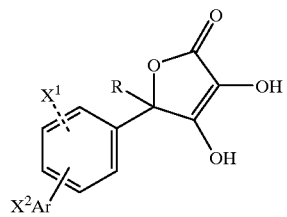

wherein

R is hydrogen, a lower alkyl group optionally substituted by one or more halo groups, a cycloalkyl group, or an aryl group optionally substituted by one or more halo, alkyl of one to eight carbon atoms, alkoxy of one to eight carbon atoms, cycloalkyl, nitro or trifluoromethyl groups;

Ar is an aromatic or heteroaromatic ring substituted by $X^2$, $X^2$ being one or more halo, alkyl of one to eight carbon atoms, alkoxy of one to eight carbon atoms, cycloalkyl, nitro or trifluoromethyl groups;

$X^1$ is optionally one or more halo, alkyl of one to eight carbon atoms, alkoxy of one to eight carbon atoms, cycloalkyl, nitro or trifluoromethyl groups;

or a pharmaceutically acceptable salt thereof.

2. The compound of claim 1 wherein said Ar group is an aromatic ring.

3. The compound of claim 2 wherein said aromatic ring is phenyl or naphthyl.

4. The compound of claim 1 wherein said Ar group is a heteroaromatic ring.

5. The compound of claim 4 wherein said heteroaromatic ring is thienyl, furyl, or pyridyl.

6. The compound of claim 1 wherein R is methyl.

7. The compound of claim 6 wherein said compound is racemic 5-[(4'-fluoro-1,1'-biphenyl)-4-yl]-5-methyl-3,4-dihydroxy-2(5H)-furanone;

(S)-(+)-5-[(4'-fluoro-1,1'-biphenyl)-4-yl]-5-methyl-3,4-dihydroxy-2(5H)-furanone;

(R)-(−)-5-[(4'-fluoro-1,1'-biphenyl)-4-yl]-5-methyl-3,4-dihydroxy-2(5H)-furanone;

racemic 5-[(4'-bromo-1,1'-biphenyl)-4-yl]-5-methyl-3,4-dihydroxy-2(5H)-furanone;

(S)-(+)5-[(4'-bromo-1,1'-biphenyl)-4-yl]-5-methyl-3,4-dihydroxy-2(5H)-furanone;

(R)-(−)-5-[(4'-bromo-1,1'-biphenyl)-4-yl]-5-methyl-3,4-dihydroxy-2(5H)-furanone;

racemic 5-[(4'-chloro-1,1'-biphenyl)-4-yl]-5-methyl-3,4-dihydroxy-2(5H)-furanone, (S)-(+)5-[(4'-chloro-1,1'-biphenyl)-4-yl]-5-methyl-3,4-dihydroxy-2(5H)-furanone; or (R)-(−)-5-[(4'-chloro-1,1'-biphenyl)-4-yl]-5-methyl-3,4-dihydroxy-2(5H)-furanone.

8. The compound of claim 1 wherein R is hydrogen.

9. The compound of claim 8 wherein said compound is

5-[(4'-fluoro-1,1'-biphenyl)-4-yl]-3,4-dihydroxy-2(5H)-furanone;

5-[(4'-bromo-1,1'-biphenyl)-4-yl]-3,4-dihydroxy-2(5H)-furanone;

5-[(4'-chloro-1,1'-biphenyl)-4-yl]-3,4-dihydroxy-2(5H)-furanone;

5-[(3',4'-dichloro-1,1'-biphenyl)-4-yl]-3,4-dihydroxy-2 (5H)-furanone; or

5-[(2',4'-dichloro-1,1'-biphenyl)-4-yl]-3,4-dihydroxy-2 (5H)-furanone.

10. The compound of claim 1 wherein $X^2$ is a halo group.

11. The compound of claim 10 wherein said compound is

5-[(3,4'-dichloro-1,1'-biphenyl)-4-yl]-3,4-dihydroxy-2 (5H)-furanone;

5-[(3,4'-dichloro-1,1'-biphenyl)-4-yl]-5-methyl-3,4-dihydroxy-2(5H)-furanone;

5-[(3,4'-dichloro-1,1'-biphenyl)-4-yl]-5-phenyl-3,4-dihydroxy-2(5H)-furanone;

5-[(3,4'-dichloro-1,1'-biphenyl)-4-yl]-5-cyclohexyl-3,4-dihydroxy-2(5H)-furanone;

5-[(3,4'-dichloro-1,1'-biphenyl)-4-yl]-5-(4-nitrophenyl)-3,4-dihydroxy-2(5H)-furanone;

5-[(3-chloro-4'-methyl-1,1'-biphenyl)-4-yl]-3,4-dihydroxy-2(5H)-furanone;

5-[(3-chloro-4'-methyl-1,1'-biphenyl)-4-yl]-5-methyl-3,4-dihydroxy-2(5H)-furanone;

5-[(3-chloro-4'-methyl-1,1'-biphenyl)-4-yl]-5-phenyl-3,4-dihydroxy-2(5H)-furanone;

5-[(3-chloro-4'-methyl-1,1'-biphenyl)-4-yl]-5-cyclohexyl-3,4-dihydroxy-2(5H)-furanone; or 5-[(3-chloro-4'-methyl-1,1'-biphenyl)-4-yl]-5-(4-nitrophenyl)-3,4-dihydroxy-2(5H)-furanone.

12. A method of treating a pathology in which reactive oxygen species and inflammatory mediators are contributing deleterious factors which comprises administration to a patient in need of such therapy an effective amount of a racemic or optically active compound of the formula

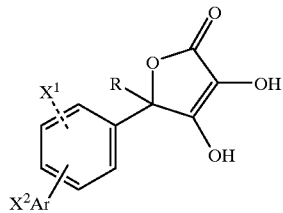

wherein

R is hydrogen, a lower alkyl group optionally substituted by one or more halo groups, a cycloalkyl group, or an aryl group optionally substituted by one or more halo, alkyl of one to eight carbon atoms, alkoxy of one to eight carbon atoms, cycloalkyl, nitro or trifluoromethyl groups;

Ar is an aromatic or heteroaromatic ring substituted by $X^2$, $X^2$ being one or more halo, alkyl of one to eight carbon atoms, alkoxy of one to eight carbon atoms, cycloalkyl, nitro or trifluoromethyl groups;

$X^1$ is optionally one or more halo, alkyl of one to eight carbon atoms, alkoxy of one to eight carbon atoms, cycloalkyl, nitro or trifluoromethyl groups;

or a pharmaceutically acceptable salt thereof.

13. The method of claim 12 wherein said Ar group is an aromatic ring.

14. The method of claim 13 wherein said aromatic ring is phenyl or naphthyl.

15. The method of claim 12 wherein said Ar group is a heteroaromatic ring.

16. The method of claim 15 wherein said heteroaromatic ring is thienyl, furyl, or pyridyl.

17. The method of claim 12 wherein R is methyl.

18. The method of claim 12 wherein said compound is racemic 5-[(4'-fluoro-1,1'-biphenyl)-4-yl]-5-methyl-3,4-dihydroxy-2(5H)-furanone;

(S)-(+)-5-[(4'-fluoro-1,1'-biphenyl)-4-yl]-5-methyl-3,4-dihydroxy-2(5H)-furanone;

(R)-(−)-5-[(4'-fluoro-1,1'-biphenyl)-4-yl]-5-methyl-3,4-dihydroxy-2(5H)-furanone;

racemic 5-[(4'-bromo-1,1'-biphenyl)-4-yl]-5-methyl-3,4-dihydroxy-2(5H)-furanone;

(S)-(+)5-[(4'-bromo-1,1'-biphenyl)-4-yl]-5-methyl-3,4-dihydroxy-2(5H)-furanone;

(R)-(−)-5-[(4'-bromo-1,1'-biphenyl)-4-yl]-5-methyl-3,4-dihydroxy-2(5H)-furanone;

racemic 5-[(4'-chloro-1,1'-biphenyl)-4-yl]-5-methyl-3,4-dihydroxy-2(5H)-furanone, (S)-(+) 5-[(4'-chloro-1,1'-biphenyl)-4-yl]-5-methyl-3,4-dihydroxy-2(5H)-furanone; or (R)-(−)-5-[(4'-chloro-1,1'-biphenyl)-4-yl]-5-methyl-3,4-dihydroxy-2(5H)-furanone.

19. The method of claim 12 wherein R is hydrogen.

20. The method of claim 19 wherein said compound is

5-[(4'-fluoro-1,1'-biphenyl)-4-yl]-3,4-dihydroxy-2(5H)-furanone;

5-[(4'-bromo-1,1'-biphenyl)-4-yl]-3,4-dihydroxy-2(5H)-furanone;

5-[(4'-chloro-1,1'-biphenyl)-4-yl]-3,4-dihydroxy-2(5H)-furanone;

5-[(3',4'-dichloro-1,1'-biphenyl)-4-yl]-3,4-dihydroxy-2(5H)-furanone; or

5-[(2',4'-dichloro-1,1'-biphenyl)-4-yl]-3,4-dihydroxy-2(5H)-furanone.

21. The method of claim 12 wherein $X^2$ is a halo group.

22. The method of claim 21 wherein said compound is

5-[(3,4'-dichloro-1,1'-biphenyl)-4-yl]-3,4-dihydroxy-2(5H)-furanone;

5-[(3,4'-dichloro-1,1'-biphenyl)-4-yl]-5-methyl-3,4-dihydroxy-2(5H)-furanone;

5-[(3,4'-dichloro-1,1'-biphenyl)-4-yl]-5-phenyl-3,4-dihydroxy-2(5H)-furanone;

5-[(3,4'-dichloro-1,1'-biphenyl)-4-yl]-5-cyclohexyl-3,4-dihydroxy-2(5H)-furanone;

5-[(3,4'-dichloro-1,1'-biphenyl)-4-yl]-5-(4-nitrophenyl)-3,4-dihydroxy-2(5H)-furanone;

5-[(3-chloro-4'-methyl-1,1'-biphenyl)-4-yl]-3,4-dihydroxy-2(5H)-furanone;

5-[(3-chloro-4'-methyl-1,1'-biphenyl)-4-yl]-5-methyl-3,4-dihydroxy-2(5H)-furanone;

5-[(3-chloro-4'-methyl-1,1'-biphenyl)-4-yl]-5-phenyl-3,4-dihydroxy-2(5H)-furanone;

5-[(3-chloro-4'-methyl-1,1'-biphenyl)-4-yl]-5-cyclohexyl-3,4-dihydroxy-2(5H)-furanone; or 5-[(3-chloro-4'-methyl-1,1'-biphenyl)-4-yl]-5-(4-nitrophenyl)-3,4-dihydroxy-2(5H)-furanone.

23. The method of claim 12 wherein said pathology comprises an acute or chronic inflammatory disorder.

24. The method of claim 23 wherein said acute or chronic inflammatory disorder is asthma, rheumatoid arthritis, inflammatory bowel disease, or acute respiratory distress syndrome.

25. The method of claim 12 wherein said pathology comprises a neurodegenerative disorder.

26. The method of claim 25 wherein said neurodegenerative disorder is Alzheimer disease, Parkinson disease, amyotrophic lateral sclerosis, traumatic brain injury or multiple sclerosis.

27. The method of claim 12 wherein said pathology comprises a cardiovascular disease.

28. The method of claim 27 wherein said cardiovascular disease is atherosclerosis.

29. The method of claim 12 wherein said pathology comprises a viral disease.

30. The method of claim 29 wherein said viral disease is AIDS.

31. The method of claim 12 wherein said pathology comprises a skin disease.

32. The method of claim 31 wherein said skin disease is psoriasis, sunburn, or premature aging of the skin.

33. The method of claim 12 wherein said pathology comprises an eye disease.

34. The method of claim 33 wherein said eye disease is glaucoma, cataract, senile macular degeneration, inflammatory eye conditions, trauma, post-traumatic eye disorders, diabetic retinopathy, or an eye infection.

35. A pharmaceutical composition comprising a compound of claim 1 and a pharmaceutically acceptable carrier.

* * * * *